(12) United States Patent
Hulliger et al.

(10) Patent No.: US 10,335,213 B2
(45) Date of Patent: Jul. 2, 2019

(54) BONE PLATE WITH A BONE SCREW

(71) Applicant: KÖNIGSEE IMPLANTATE GMBH, Allendorf OT Aschau (DE)

(72) Inventors: Urs Hulliger, Deitingen (CH); Michael Riese, Gehren (DE); Tino Harz, Königsee-Rottenbach (DE); Frank Orschler, Erfurt (DE)

(73) Assignee: KÖNIGSEE IMPLANTATE GMBH, Allendorf OT Aschau (DE)

( * ) Notice: Subject to any disclaimer, the term of this patent is extended or adjusted under 35 U.S.C. 154(b) by 135 days.

(21) Appl. No.: 15/546,594

(22) PCT Filed: Mar. 11, 2016

(86) PCT No.: PCT/EP2016/055237
§ 371 (c)(1),
(2) Date: Jul. 26, 2017

(87) PCT Pub. No.: WO2016/142502
PCT Pub. Date: Sep. 15, 2016

(65) Prior Publication Data
US 2018/0008326 A1    Jan. 11, 2018

(30) Foreign Application Priority Data

Mar. 11, 2015   (DE) .................. 10 2015 003 087
Feb. 29, 2016   (DE) .................. 10 2016 002 444

(51) Int. Cl.
*A61B 17/80*    (2006.01)
*A61B 17/86*    (2006.01)

(52) U.S. Cl.
CPC ...... *A61B 17/8057* (2013.01); *A61B 17/8605* (2013.01)

(58) Field of Classification Search
CPC .................. A61B 17/8057; A61B 17/8605
See application file for complete search history.

(56) References Cited

U.S. PATENT DOCUMENTS 6,322,562 B1   11/2001  Wolter .......................... 606/62
9,161,795 B2   10/2015  Clasbrummel et al.
(Continued)

FOREIGN PATENT DOCUMENTS

DE     198 58 889 A1    6/2000
DE   10 2005 042 7      1/2007
(Continued)

OTHER PUBLICATIONS

A copy of the Notification Concerning Transmittal of Copy of International Preliminary Report on Patentability (Chapter I of the Patent Cooperation Treaty), in English, dated Sep. 21, 2017, which was issued by the International Bureau of Wipo in Applicant's corresponding international PCT application having U.S. Appl. No. PCT/EP2016/055237, filed on Mar. 11, 2016.
(Continued)

*Primary Examiner* — Christian A Sevilla
(74) *Attorney, Agent, or Firm* — Bodner & O'Rourke, LLP; Gerald T. Bodner; Christian P. Bodner

(57) ABSTRACT

The invention relates to an osteosynthesis device with a bone plate and with at least one bone screw, wherein the bone plate has at least one through-hole with a conical inner thread formed at least in part in the through-hole. Moreover, the bone screw has a screw shank and also a screw head with a conical thread, with the possibility of forming a connection at a variable and stable angle between bone screw and bone plate by receiving the screw head with conical outer thread in the respective through-hole of the bone plate. According to the invention, the thread in the screw head has a first portion A with a first conicity and a second portion B with a second conicity, wherein a zone of discontinuity with respect to the conicity is present between the first portion A and the second portion B.

14 Claims, 14 Drawing Sheets

(56) References Cited

U.S. PATENT DOCUMENTS

Figure 1:
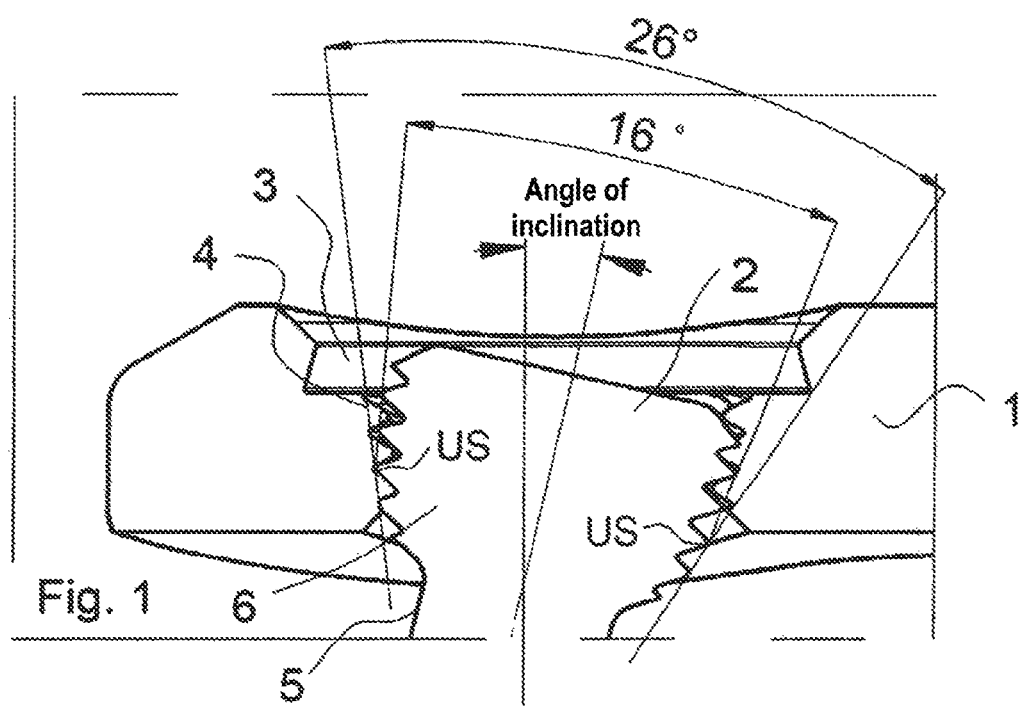

| | | | |
|---|---|---|---|
| 10,130,407 B2* | 11/2018 | Castaneda | A61B 17/8645 |
| 2005/0010226 A1* | 1/2005 | Grady, Jr. | A61B 17/746 |
| | | | 606/281 |
| 2005/0049594 A1* | 3/2005 | Wack | A61B 17/1728 |
| | | | 606/86 B |
| 2007/0233123 A1* | 10/2007 | Ahmad | A61B 17/863 |
| | | | 606/307 |
| 2010/0137919 A1 | 6/2010 | Wolter | 606/308 |
| 2013/0138156 A1 | 5/2013 | Derouet | 606/289 |

FOREIGN PATENT DOCUMENTS

| | | |
|---|---|---|
| DE | 10 2006 060 9 | 7/2008 |
| DE | 198 58 889 B4 | 8/2008 |
| DE | 10 2005 042 7 | 8/2009 |
| DE | 10 2010 038 9 | 2/2012 |
| EP | 2 559 392 | 9/2014 |
| WO | WO 2008/077491 | 7/2008 |
| WO | WO 2008/115318 | 9/2008 |
| WO | WO 2011/076205 | 6/2011 |

OTHER PUBLICATIONS

A copy of the English translation of the International Preliminary Report on Patentability (Chapter I of the Patent Cooperation Treaty), dated Sep. 12, 2017, which was issued by the International Bureau of Wipo in Applicant's corresponding international PCT application having U.S. Appl. No. PCT/EP2016/055237, filed on Mar. 11, 2016.

Applicant's a copy of the Written Opinion of the International Searching Authority, in English, dated Jun. 10, 2016, which was issued by the International Bureau of Wipo in corresponding international PCT application having U.S. Appl. No. PCT/EP2016/055237, filed on Mar. 11, 2016.

A copy of the International Search Report, in English, dated Jun. 10, 2016, which was issued by the International Bureau of Wipo in Applicant's corresponding international PCT application having U.S. Appl. No. PCT/EP2016/055237, filed on Mar. 11, 2016.

* cited by examiner

Cross-section A-A

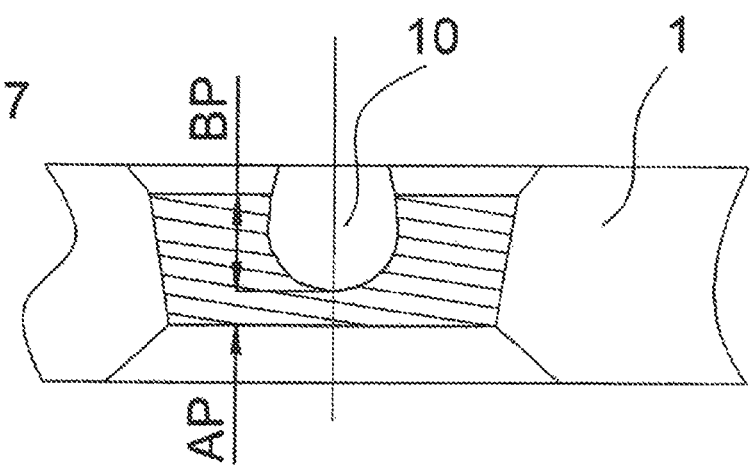

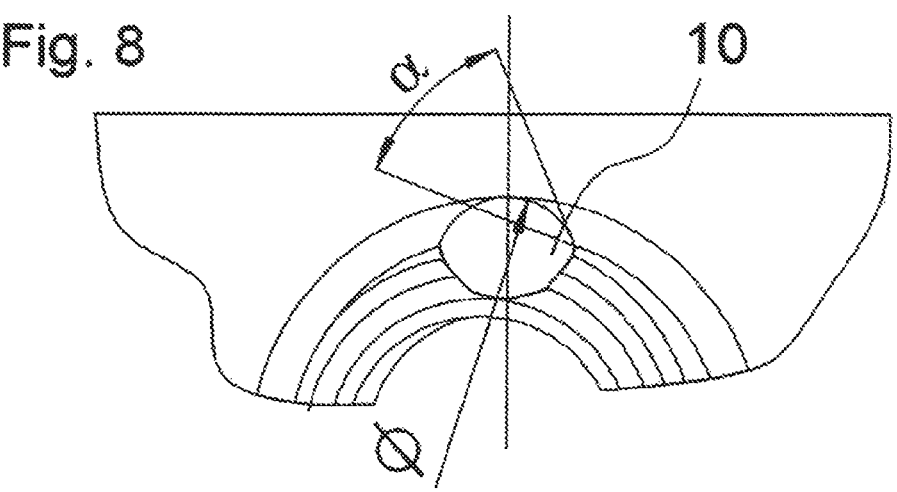

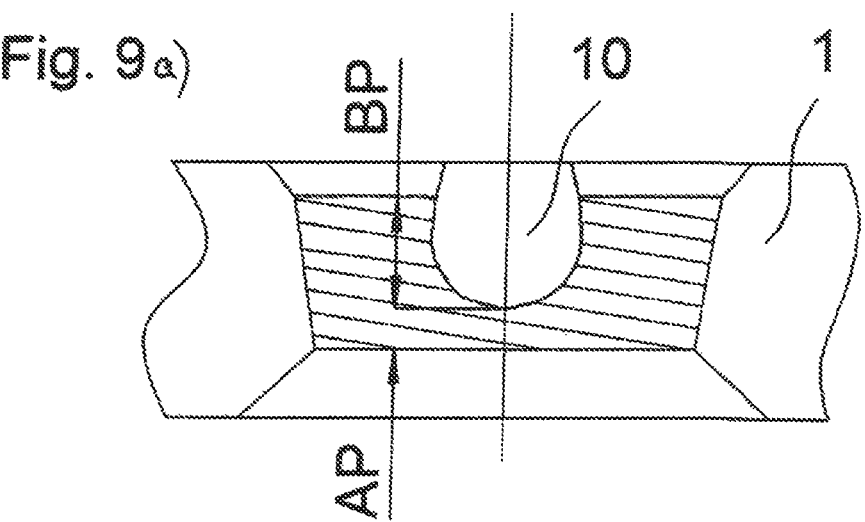

BONE PLATE WITH A BONE SCREW

The invention relates to an osteosynthesis device with a bone plate and with at least one bone screw, wherein the bone plate has at least one through-hole with a conical inner thread formed at least in part in the through-hole, the bone screw moreover has a screw shank and also a screw head with a conical thread, with the possibility of forming a connection at a variable and stable angle between bone screw and bone plate by receiving the screw head with conical outer thread in the respective through-hole of the bone plate, according to the preamble of claim 1, as well as a bone screw with a screw head and a screw shank, wherein the screw head has a conical outer thread, according to the preamble of claim 9.

A plate bore of a bone plate for osteosynthesis is already known from DE 10 2005 042 766 B4. The plate bore comprises a threaded star distributed around the circumference thereof and composed of threaded segments pointing radially toward the bore axis, and a bore recess situated in each case between two adjacent thread teeth, as well as a conical thread core diameter tapering in the screw-in direction. The plate bore has a screw head pan of a calotte shape situated on top in the screw-in direction for obtaining an extensive full-area contact between a screw head of a round head screw and a screw head pan such that the plate bore is suitable to selectively receive the round head screw or a threaded head screw in order to hereby guarantee an angle configured to be variable with respect to the longitudinal bore axis or a fixed-angle screw joint when in the screwed state.

A system for the angularly variable connection between a bone plate and one or more bone screws is already known from WO 2008/115318, wherein the respective screw heads of the bone screws comprise an outer thread whose extension corresponds to a predefined radius about an imaginary center of the screw head.

The bone plate system with a variable, angularly fixed connection according to EP 2 559 392 B1 takes a similar approach, wherein the bone plates employed therein have through-holes comprising unthreaded sections, and wherein the unthreaded sections extend continuously from the bone plate top side to the bone plate bottom side.

The bone screw according to DE 10 2006 060 933 A1 comprises a shaft that defines a longitudinal axis, and a head that is configured as a thickened section, both the shaft and the head having a thread.

In this solution of the prior art, the shaft's thread, the so-called bone thread, merges in an uninterrupted manner into the thread of a flared region of the head that adjoins the shaft. As a result, part of the head carrying the thread lies in the osseous tissue, whereby a larger bone screw-bone contact surface is supposed to be formed and the distribution and transmission of loads and forces are improved.

In the bone fixation system according to DE 198 58 889 B4, a connecting support in the form of a bone plate having at least one through-hole is present. Furthermore, at least one bone screw inserted in a through-hole is present, a mutual orientation being given at various angles. Below the seating surfaces of bone screw and connecting support, the fixing means comprise a thread connection formed by deforming a preformed thread below at least one of the seating surfaces by screwing in the bone screw at a defined angle.

An osteosynthesis device with a bone plate and at least one bone screw is already known from the generic DE 10 2010 038 949 A1, wherein the bone plate comprises at least one threaded bore, and the bone screw is provided with a screw head having an outer thread, the threaded bore moreover comprising a multi-start internal thread, and the bone screw comprising a single-start external thread.

According to the problem therein, the bone screw should be able to be inserted into the bone plate's threaded bore at various angles, and there should be the option to transmit high forces to the bone plate. According to the teaching therein, it is provided for the pitches of the bone screw's external thread and that of the threaded bore's internal thread to be of equal size, whereby a tensioning should be achieved after the engagement of the threads which initiates the angular stability of the joint. To facilitate the inserting of the prior art bone screw into the bone plate at various angles, it is provided for the bone screw to have a conical external thread.

For solving the task according to DE 10 2010 038 949 A1, it is in particular provided for the bone screw's external thread to have at least one incision extending conically the bone screw's longitudinal axis. In a preferred embodiment, a plurality of incisions, preferentially four incisions are provided which are regularly distributed over the circumference of the bone screw's external thread. The incisions are configured to be of a circular segment shape, the axis of the incision being preferably in parallel to the external thread's surface line. The purpose of the above-mentioned incisions is to enable the threads to engage preferably immediately after placing the external thread onto the internal thread, without the need to unnecessarily rotate the bone screw.

From the aforementioned, it is the task of the invention to propose an improved osteosynthesis device with a bone plate and with at least one bone screw, wherein the bone plate has at least one through-hole with a conical inner thread formed at least in part in the through-hole. The improved osteosynthesis device is intended to have a favorable insertion torque and a high locking stability. In particular, it is to be ensured that a very stable locking corresponding to at least that which exists in osteosynthesis devices having not an angle-variable configuration of the respective screw joints, is given even when the bone screw is introduced into the through-hole perpendicular to the bone plate's longitudinal axis.

The solution of the task of the invention is performed by a feature combination according to the teaching of claim 1 and the osteosynthesis device described there which is composed of a bone plate and at least one bone screw, and a bone screw with a screw head and a screw shank, wherein the screw head has a conical outer thread, according to the feature combination of claim 9, the dependent claims representing at least appropriate configurations and further developments.

Accordingly, an osteosynthesis device with a bone plate and with at least one bone screw is taken as a basis, wherein the bone plate has at least one through-hole with a conical outer thread formed at least in part in the through-hole. The definition of bone plate and through-hole with a conical thread formed at least in part should not be understood as limiting but there may be, of course, completely different, anatomically adapted bone plates with a plurality of through-holes, wherein at least one of the through-holes has the mentioned conical inner thread.

It is decisive for the bone screw to have a screw shank and also a screw head with a conical outer thread, with the possibility of forming a connection at a variable and stable angle between bone screw and bone plate by receiving the screw head with the conical outer thread in the respective through-hole of the bone plate.

According to the invention, the outer thread in the screw head is particularly configured in that a first portion A with a first conicity and a second portion B with a second conicity are provided, wherein a zone of discontinuity with respect to the conicity is present between the first portion A and the second portion B.

The zone of discontinuity means in this case the transition from the first conicity to the second conicity which is abrupt. The point of discontinuity may in this case have a first point of discontinuity with a subsequent continuous progress, and following this, a second point of discontinuity, with no conicity of the thread being present between the first and second points of discontinuity.

It is moreover within the meaning of the invention that the first and second portions are followed by a third portion with again a different conicity, without departing from the basic inventive idea.

According to the invention, the first portion A is directed toward the end of the screw head, and the second portion B toward the screw shank. The end of the screw head means the screw head side which serves to receive or rather to place or insert a tool for operating the screw.

In a particularly inventive manner the thread in the screw head is formed as a biconical or multiple conical thread, wherein the cone in the first portion A is realized to be smaller than the cone in the second portion B.

The smaller cone or cone angle substantially corresponds to the conicity of the thread in the through-hole.

In a preferred further development of the invention, the cone angle of the first conicity substantially is 10° to 20°, preferentially 14° to 16°, and the cone angle of the second conicity substantially is 23° to 30°, preferentially 24° to 26°.

At an angle of inclination of up to 15° that is preferentially deviating from the bone plate's vertical line, an autonomous insertion of the bone screw into the through-hole thread will take place due to the larger cone angle and thus the steeper cone.

The osteosynthesis device moreover comprises specifically configured inner threads in the through-hole or through-holes such that a plurality of recesses in the form of non-threaded clearances that are arranged to be distributed on the circumference side are formed to be oriented toward the bone plate top or insertion side, which may even extend only over a part of the depth of the respective through-hole. Basically, however, the tendency should be maintained that the thread discontinuity decreases toward the plate bottom.

This means that the inner thread in the respective through-hole of the bone plate is formed to be substantially free from discontinuity in the area of the bone plate bottom.

Moreover, according to the invention is a bone screw with a screw head and a screw shank, wherein the screw head has a conical outer thread, and the thread in the screw head has a first portion A with a first conicity and a second portion B with a second conicity, wherein a zone of discontinuity with respect to the conicity is present between the first portion A and the second portion B. The bone screw according to the invention accordingly has a first portion A directed toward the end of the screw head, and a second portion B directed toward the screw shank. The thread in the screw head is formed as a biconical thread, wherein the cone in the first portion A is smaller than the cone in the second portion B.

In particular, the cone angle of the first conicity substantially is 10° to 20°, preferentially 14° to 16°, and the cone angle of the second conicity substantially is 23° to 30°, preferentially 24° to 26°.

The invention will be explained in more detail based on an exemplary embodiment and with reference to figures.

Figure 2:
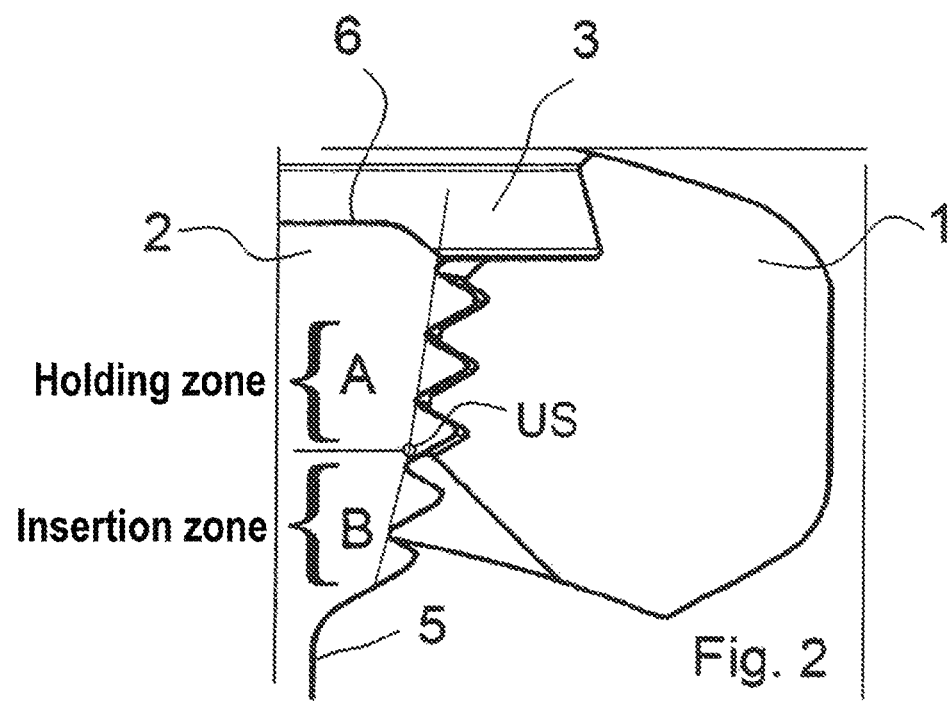
Figure 3:
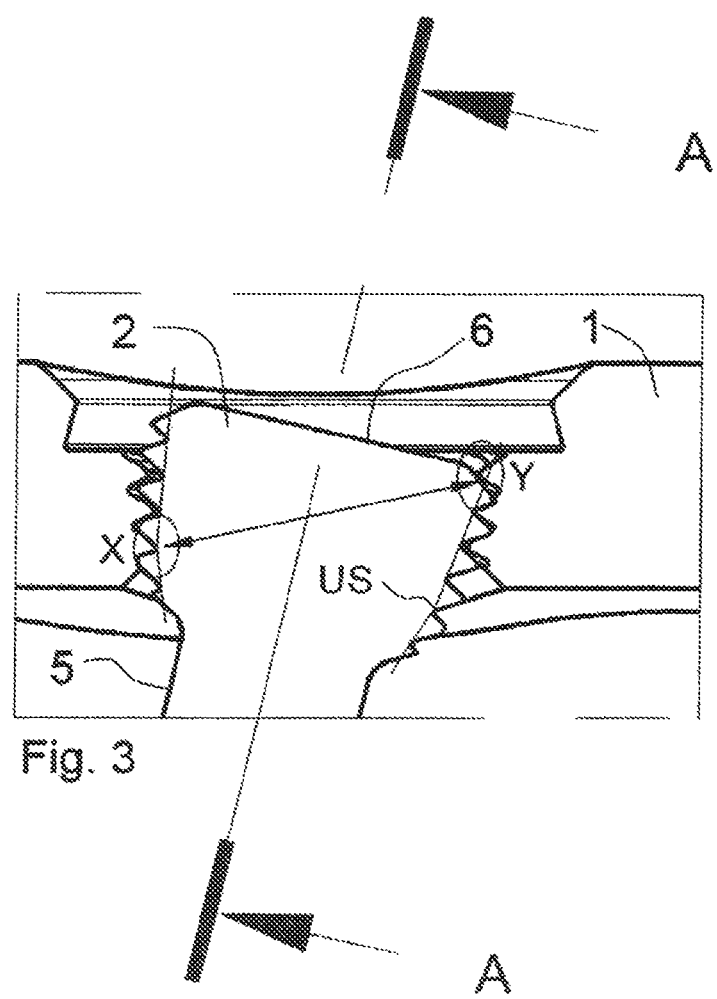
Figure 4:
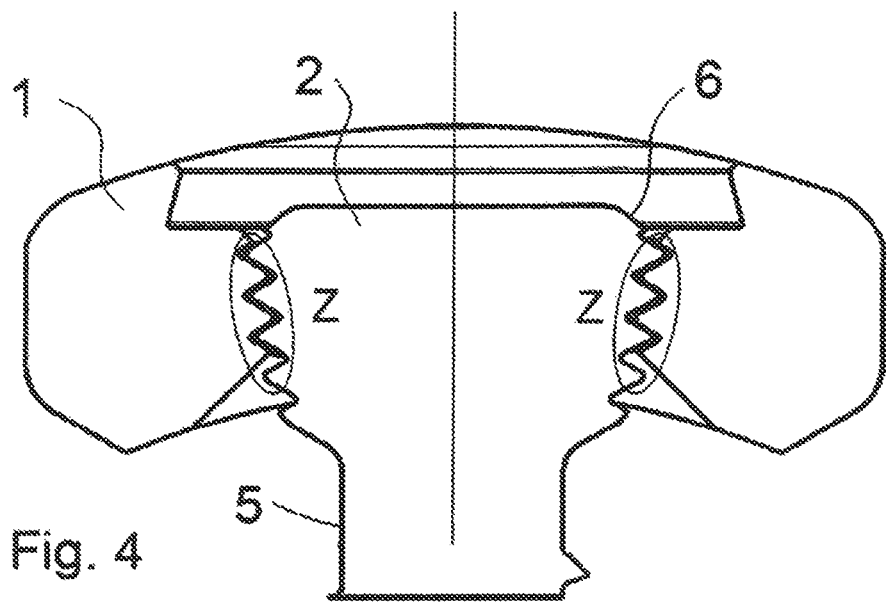
Figure 5:
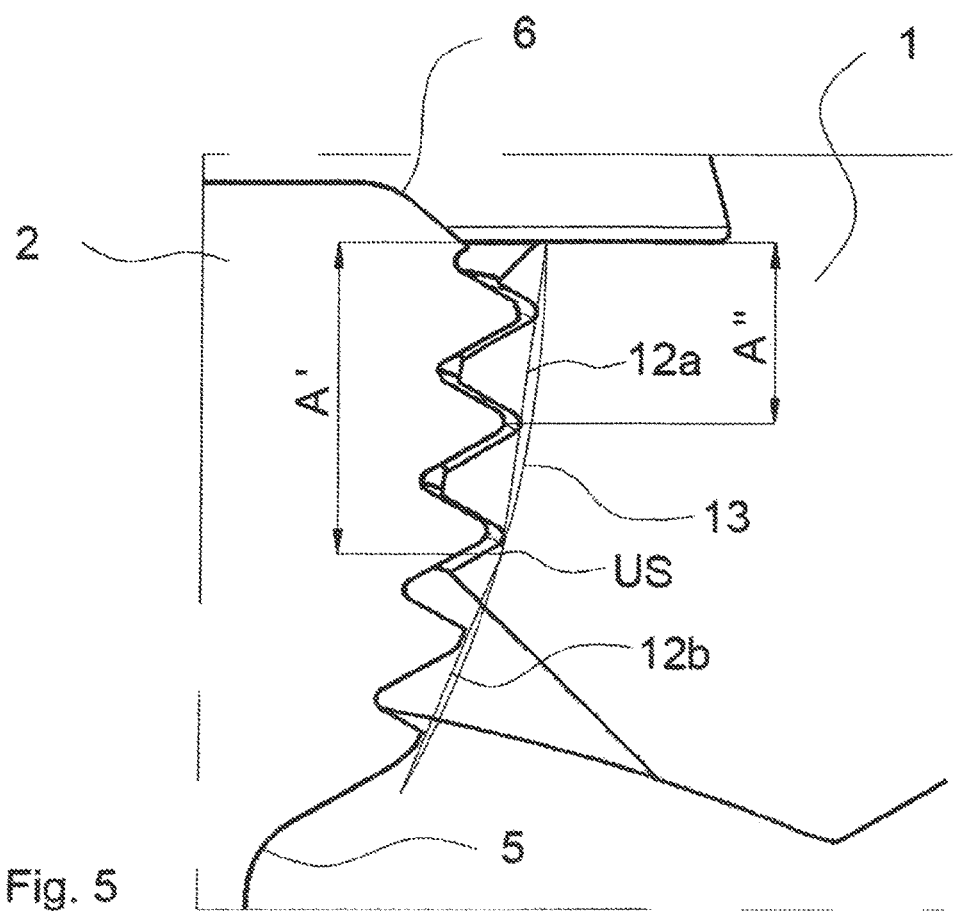
Figure 6:
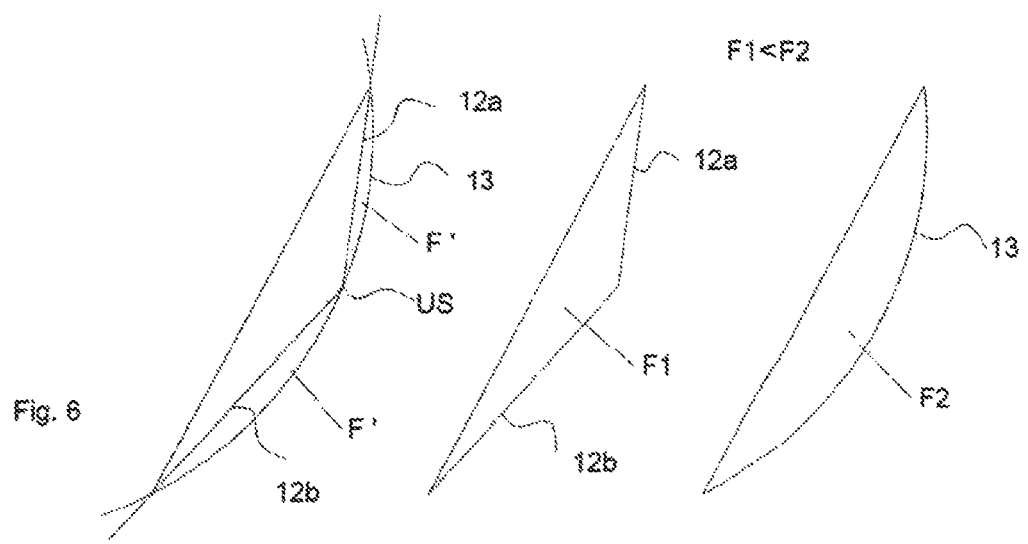
Figure 9B:
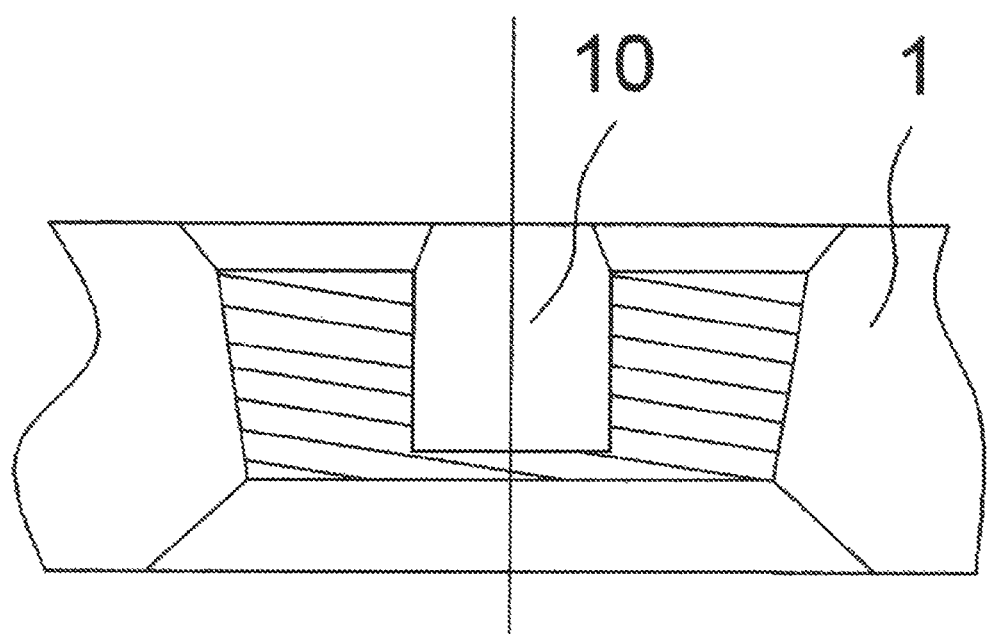
Figure 9C:
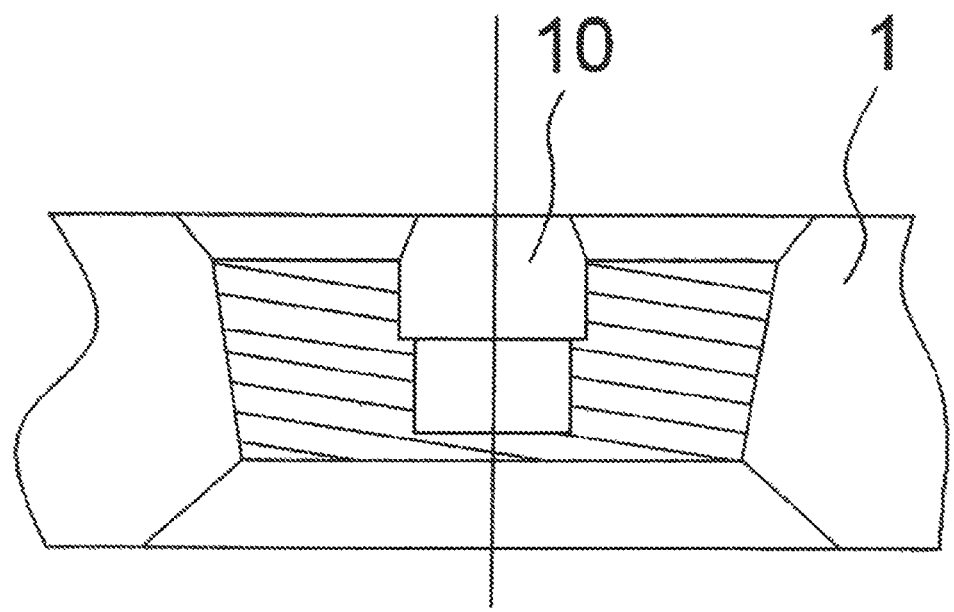
Figure 9D:
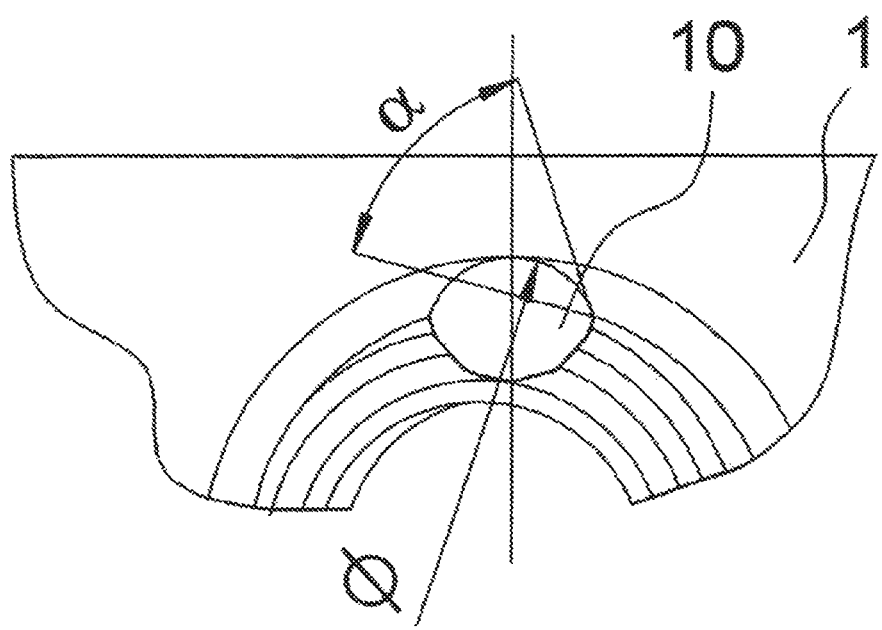
Figure 9E:
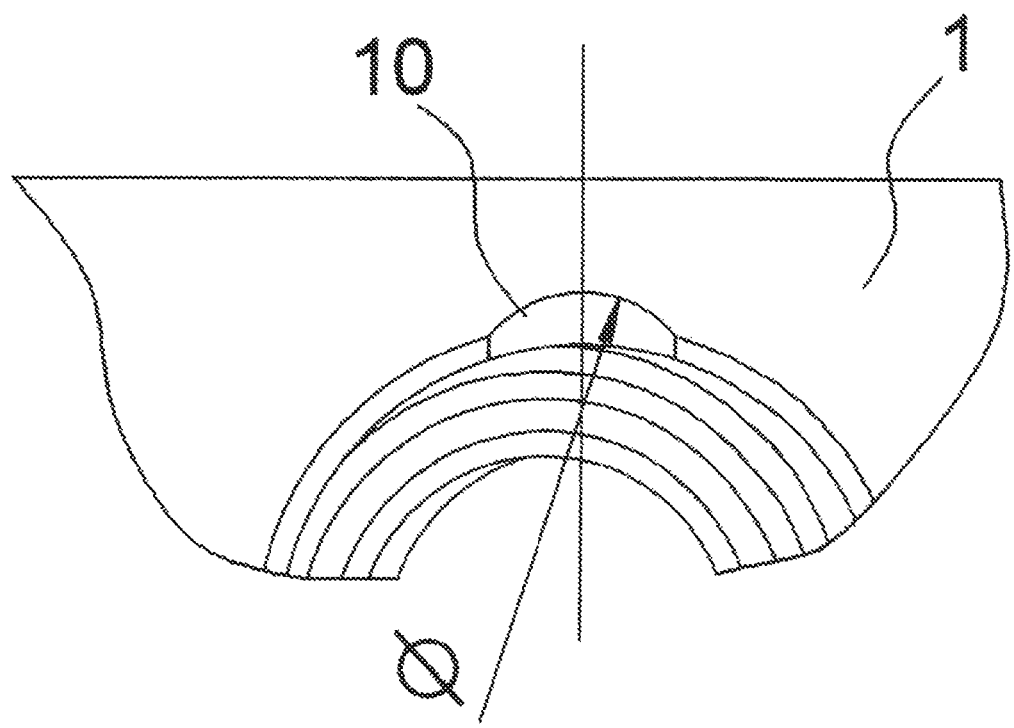
Figure 9F:
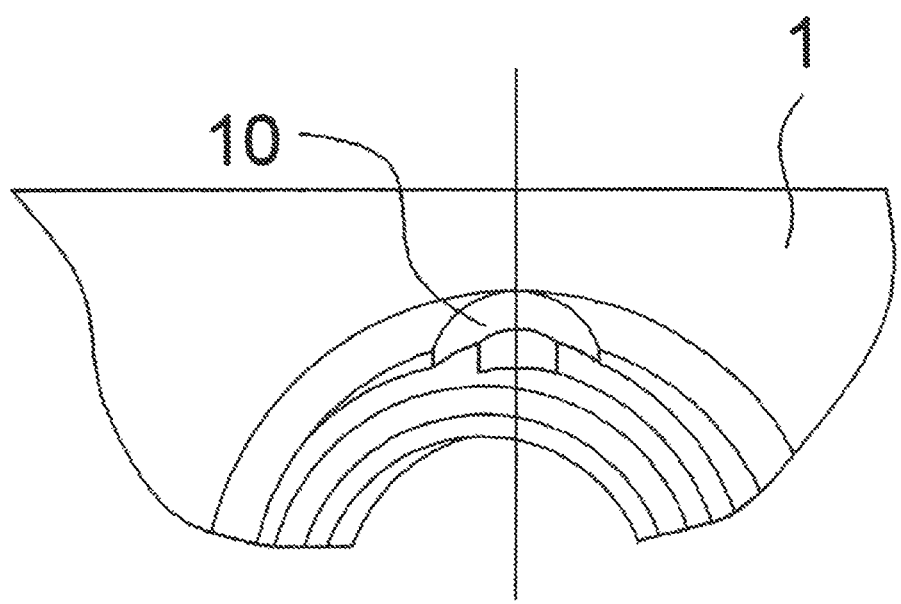

Shown are in:

FIG. 1 a sectional view of the osteosynthesis device according to the invention with a bone plate and with a bone screw, wherein the bone plate has a through-hole with a conical inner thread;

FIG. 2 a detailed view based on FIG. 1, including the portions A and B, wherein portion A is defined as the holding zone and portion B as the insertion zone, namely in the meaning of an autonomous insertion of the corresponding bone screw into the thread in the respective through-hole;

FIG. 3 a sectional view with the screw thread visibly interlocking in the plane of inclination via pronounced corners in the regions X and Y;

FIG. 4 a sectional view along the lines A-A as per FIG. 3 with an interlocking that is visible there across the entire cone area in the regions Z, wherein the sectional view as per FIG. 4 is selected to be at an angle of 90° to the representation as per FIG. 3;

FIG. 5 a sectional view of the interlocking at an improved holding torque;

FIG. 6 an explanation drawing relating to the cross-sections of displacement when a fixed connection is formed between the bone screw and bone plate;

FIG. 7 a sectional view through a bone plate with a through-hole according to the invention which has a conical inner thread, and with a clearance being provided in the form of a non-threaded recess, FIG. 8 a representation similar to that of FIG. 7 but in a partially broken and partially perspective view, and FIGS. 9*a* to *f* various options of the configuration of clearances in the form of non-threaded recesses.

The osteosynthesis device described in the Figures is based on a bone plate 1 and at least one bone screw 2, wherein the bone plate 1 has at least one through-hole 3 with a conical inner thread 4 formed at least in part in the through-hole.

The bone screw 2 has a screw shank 5 as well as a screw head 6.

The screw head 6 has a specific conical thread, with the possibility of forming a connection at a variable and stable angle between bone screw 2 and bone plate 1 by receiving the screw head 6 with the specific conical outer thread in the respective through-hole 3 of the bone plate 1.

The thread in the screw head 6 has a first portion A (see FIG. 2), referred to as a holding zone there, with a first conicity and a second portion B, referred to as an insertion zone there, with a second conicity, wherein a zone of discontinuity US with respect to the conicity is present between the first portion A and the second portion B.

The first portion A is directed toward the end of the screw head and the second portion B toward the screw shank 5.

In a preferred embodiment of the cone angles, as illustrated in FIG. 1, the conical thread in the bone plate 1 has a conicity of 16°, wherein the thread in the bone plate 1 is realized to be double-threaded.

In a corresponding design, the conical thread in the bone plate 1 or through-hole 3 of the bone plate 1 further has five circumferentially distributed clearances, e.g. in a V shape, at the thread periphery, as is also shown on the basis of FIGS. 7 and 8.

According to the illustration in the Figures, in particular FIG. 1, the screw head 6 has a double conical head thread, namely from 16°, on the one hand, and 22° to 26°, on the other.

The smaller cone of 16° on the head thread corresponds to the cone angle of 16° in the through-hole 3 of the bone plate 1.

The screw head profile corresponds to the profile of the thread in the bone plate 1. The angle of inclination illustrated in FIG. 1 may be selected in the range from 0° to 15°. In the case of an angle of inclination of 0°, the bone screw is inserted perpendicular to the bone plate's 1 longitudinal axis in the threaded through-hole 3.

Due to the second, steeper cone of 22° to 26° at the screw head 6, referred to as B in FIG. 2, an autonomous insertion of the bone screw 2 into the thread in the respective through-hole 3 of the bone plate 1 is ensured at a large angle of inclination of the bone screw 2 to the bone plate 1.

Due to the autonomous insertion of the bone screw into the thread in the through-hole 3 of the bone plate 1, positive interlocking of the screw thread and the plate thread in the plane of inclination of the screw is achieved according to the illustration as per FIG. 3, on the one hand, and positive interlocking of the screw thread and the plate thread according to section A-A as per FIG. 4 (offset by 90°) is achieved, on the other.

In the areas in between, both of the threads are connected by a partial deformation/transformation of the thread tips.

When a hardened bone screw and a bone plate that is not hardened are used in this respect, only the thread in the bone plate's through-hole will be transformed, the bone screw, in contrast, remaining undamaged. A stable locking, however, is also possible with materials of equal hardness with respect to bone plate and bone screw.

The interlocking of the screw thread takes place in the plane of inclination via the pronounced corners as per FIG. 3, regions X and Y, and at 90° thereto via the entire cone area, see FIG. 4, regions Z. Due to an optimized configuration of the conical areas with a discontinuity, an optimum holding force is achieved at a minimum insertion torque of the thread connection.

In contrast to a configuration with the radius of the screw head thread, an improved holding torque is achieved by the discontinuity in terms of a "corner-type" configuration. The conical area which takes effect when the screw is completely inserted, is significantly improved as compared to a variation having a radius according to the state of the art such as is symbolized by FIG. 5 along with the short explanations there. Thus, portion A' is significantly larger than portion A".

With regard to FIGS. 5 and 6, reference numeral 12A refers to the envelope of the thread tips of the biconical screw in thread portion A, i.e. the holding area, reference numeral 12B refers to the envelope of the thread tips of the biconical screw in thread portion B, i.e. the insertion area, and reference numeral 13 refers to the envelope of the thread tips of the screw with the screw head thread having a radius.

A further advantage of the implementation according to the invention is that the insertion torque of the bone screw in the bone plate is reduced by a decreased cross-section of displacement which is obvious from the illustrations as per FIG. 6. The surface of the triangle F1 as per FIG. 6, which represents the cross-section of displacement of the biconical screw, is smaller by the surface F' than the surface of the comparable triangle F2 which represents the cross-section of displacement of the screw with the screw head thread having a radius. The above results in a lower effort of displacement with the consequence of a lower insertion resistance when a stable locking according to the inventive solution is generated.

The structure of the clearances in the form of non-threaded recesses in the corresponding through-hole of the bone plate will be explained by means of FIGS. 7 and 8.

The clearances 10, which are arranged in the corresponding through-hole to be distributed on the circumference side, ensure that the thread of the bone screw, when in an inclined position, can fix to the plate thread, and the bone screw, when tightened, is drawn into the plate thread.

Due to the formation of the clearances 10, which is non-continuous with respect to the depth of the through-hole or the plate thickness, or the decreasing extension of the clearances toward the plate bottom, two areas are generated in the plate thread. Area BP enables the bone screw to be drawn into the plate thread. In the area BP, an improved interlocking of the bone screw in the plate thread is achieved.

Due to the non-continuous configuration or increasing reduction of the clearances, the screw's maximum turning torque through the plate is elevated since area AP has an increasingly intact, complete plate thread. In contrast to the prior art clearances having transition angles from the cut-out to the thread, the flatter wedge of the inventive solution enables the screw thread to penetrate the plate thread more easily. As a result, a transformability of the threads is improved and an otherwise interfering chip formation prevented. The configuration explained above moreover results in a reduction of the screw's insertion torque.

Based on FIGS. 7 and 8, FIG. 9 shows further optional designs and geometrical configurations of the clearances 10. The clearances 10 should be designed such that the transition angle shown in FIG. 9 is $\alpha<40°$.

The flank angle of the threads in the plate and of the respective screw usually is 60°. According to the invention, deviations from this standard configuration may be made, for example, in the range from 50° to 70°. Moreover, the thread flanks in the plate thread may have another flank angle than in the screw thread. In a screw of higher hardness, for example, a smaller angle as compared to the plate's flank angle may be selected in order to guarantee improved interlocking. In a relatively soft bone plate and a screw of higher hardness, for example, an adaptation of the flank angle of the plate of substantially 65° and of the screw of substantially 55° may be performed to optimize the screw-in behavior and the interlocking.

The invention claimed is:

1. An osteosynthesis device with a bone plate and with at least one bone screw, wherein the bone plate has at least one through-hole with a conical inner thread formed at least in part in the through-hole, the bone screw moreover has a screw shank and also a screw head with a conical thread, with the possibility of forming a connection at a variable and stable angle between bone screw and bone plate by receiving the screw head with conical outer thread in the respective through-hole of the bone plate, characterized in that the thread in the screw head has a first portion with a first conicity and a second portion with a second conicity, wherein a zone of discontinuity with respect to the conicity is present between the first portion and the second portion.

2. The osteosynthesis device according to claim 1, characterized in that the first portion is directed toward the end of the screw head, and the second portion toward the screw shank.

3. The osteosynthesis device according to claim 1, characterized in that the thread in the screw head is formed as a biconical thread, wherein the cone in the first portion is realized to be smaller than the cone in the second portion.

4. The osteosynthesis device according to claim 3, characterized in that the smaller cone or cone angle substantially corresponds to the conicity of the thread in the through-hole.

5. The osteosynthesis device according to claim 1, characterized in that the cone angle of the first conicity substantially is 10° to 20° and the cone angle of the second conicity substantially is 23° to 30°.

6. The osteosynthesis device according to claim 5, characterized in that at an angle of inclination of up to 15° that is deviating from the bone plate's vertical line, an autonomous insertion of the bone screw into the conical thread in the through-hole will take place due to the larger cone angle.

7. The osteosynthesis device according to claim 1, characterized in that the inner thread in the respective through-hole of the bone plate has a plurality of clearances in the form of non-threaded recesses that are directed toward the bone plate top or toward the insertion side, which are arranged to be distributed on the circumference side.

8. The osteosynthesis device according to claim 7, characterized in that the inner thread in the respective through-hole of the bone plate is formed to be free from discontinuity in the area of the bone plate bottom.

9. A bone screw with a screw head and a screw shank, wherein the screw head has a conical outer thread, characterized in that the thread in the screw head has a first portion with a first conicity and a second portion with a second conicity, wherein a zone of discontinuity with respect to the conicity is present between the first portion and the second portion.

10. The bone screw according to claim 9, characterized in that the first portion is directed toward the end of the screw head, and the second portion toward the screw shank.

11. The osteosynthesis device according to claim 9, characterized in that the thread in the screw head is formed as a biconical thread, wherein the cone in the first portion is realized to be smaller than the cone in the second portion.

12. The osteosynthesis device according to claim 9, characterized in that the cone angle of the first conicity substantially is 10° to 20° and the cone angle of the second conicity substantially is 23° to 30°.

13. The osteosynthesis device according to claim 5, characterized in that the cone angle of the first conicity substantially is 14° to 16° and the cone angle of the second conicity substantially is 24° to 26°.

14. The osteosynthesis device according to claim 12, characterized in that the cone angle of the first conicity substantially is 14° to 16° and the cone angle of the second conicity substantially is 24° to 26°.

* * * * *